(12) United States Patent
Matsuda et al.

(10) Patent No.: US 7,736,590 B2
(45) Date of Patent: Jun. 15, 2010

(54) METHOD FOR MEASURING OXYGEN AMOUNT IN HERMETICALLY SEALED CONTAINER AND PIERCING DEVICE FOR HERMETICALLY SEALED CONTAINER USED THEREFORE

(75) Inventors: Akihiko Matsuda, Tokyo (JP); Toshihiro Akihisa, Tokyo (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 220 days.

(21) Appl. No.: 11/914,731

(22) PCT Filed: May 26, 2006

(86) PCT No.: PCT/JP2006/310574
§ 371 (c)(1),
(2), (4) Date: Nov. 16, 2007

(87) PCT Pub. No.: WO2006/126683
PCT Pub. Date: Nov. 30, 2006

(65) Prior Publication Data
US 2009/0084156 A1    Apr. 2, 2009

(30) Foreign Application Priority Data
May 27, 2005    (JP) ............................. 2005-156084

(51) Int. Cl.
*G01N 21/64* (2006.01)

(52) U.S. Cl. .................... 422/82.08; 73/19.01; 73/19.1; 73/31.05; 422/82.05; 422/82.07

(58) Field of Classification Search ............... 73/19.01, 73/19.05, 19.06, 19.1, 19.11, 23.34, 31.03, 73/31.04; 422/82.05–82.08
See application file for complete search history.

(56) References Cited

U.S. PATENT DOCUMENTS

| | | | | |
|---|---|---|---|---|
| 4,900,933 | A | * | 2/1990 | Nestor et al. .............. 250/458.1 |
| 5,034,189 | A | * | 7/1991 | Cox et al. ...................... 422/52 |
| 5,296,381 | A | * | 3/1994 | Yafuso et al. ................ 436/172 |
| 5,518,694 | A | * | 5/1996 | Bentsen .................... 422/82.08 |
| 5,633,165 | A | * | 5/1997 | Swartz ..................... 435/287.1 |
| 5,693,228 | A | * | 12/1997 | Koehler et al. .............. 210/656 |
| 5,885,843 | A | * | 3/1999 | Ayers et al. ................. 436/136 |
| 6,042,787 | A | * | 3/2000 | Pawliszyn ..................... 422/69 |
| 6,653,148 | B2 | * | 11/2003 | Trapp et al. ................. 436/172 |
| 6,664,111 | B2 | * | 12/2003 | Bentsen et al. ................ 436/68 |
| 7,338,778 | B2 | * | 3/2008 | Pitner et al. ................... 435/34 |
| 2006/0051874 | A1 | * | 3/2006 | Reed et al. .................. 436/163 |
| 2007/0203173 | A1 | * | 8/2007 | Mudumba et al. ........... 514/291 |
| 2007/0243618 | A1 | * | 10/2007 | Hatchett et al. ................ 436/1 |
| 2008/0051646 | A1 | * | 2/2008 | Papkovsky et al. .......... 600/329 |

FOREIGN PATENT DOCUMENTS

JP    01-113659 A    5/1989
(Continued)

*Primary Examiner*—David A. Rogers
(74) *Attorney, Agent, or Firm*—Sughrue Mion, PLLC (57) ABSTRACT

A method to efficiently measure the oxygen content of both the headspace and fluid within a hermetically sealed container. A container is pierced using a hollow needle with the interior space sealed from the outside and the tip of said hollow needle removed, and the interior space is made continuous with the headspace within the container. A probe of a fluorescent oxygen concentration meter is inserted through the hollow needle to the interior of the container, positioned in the headspace within the container, and the oxygen concentration of the headspace 3 is measured. The probe is inserted further so that the fluorescent material is submerged in the fluid inside the container, and the dissolved oxygen concentration inside the fluid is measured.

7 Claims, 4 Drawing Sheets

FOREIGN PATENT DOCUMENTS

| | | |
|---|---|---|
| JP | 04-176636 A | 6/1992 |
| JP | 04-218140 A | 8/1992 |
| JP | 05-223737 A | 8/1993 |
| JP | 7-58244 B2 | 6/1995 |
| JP | 10-007115 A | 1/1998 |
| JP | 10-132742 A | 5/1998 |
| JP | 11-242025 A | 9/1999 |
| JP | 3600697 B2 | 9/2004 |

* cited by examiner

METHOD FOR MEASURING OXYGEN AMOUNT IN HERMETICALLY SEALED CONTAINER AND PIERCING DEVICE FOR HERMETICALLY SEALED CONTAINER USED THEREFORE

CROSS REFERENCE TO PRIOR APPLICATIONS

This is a U.S. national phase application under 35 U.S.C. §371 of International Patent Application No. PCT/JP2006/310574, filed May 26, 2006, which claims the benefit of Japanese Application No. 2005-156084, filed May 27, 2005, both of which are incorporated by reference herein. The International Application was published in Japanese on Nov. 30, 2006 as International Publication No. WO 2006/126683 A1 under PCT Article 21(2).

TECHNICAL FIELD

The present invention is related to a method for measuring the amount of headspace in a hermetically sealed container filled with fluid and the amount of oxygen dissolved in the fluid, and to a piercing device for the container used therein.

BACKGROUND ART

In the manufacturing process of products in which a fluid is hermetically sealed in a container, such as in canned foods, in order to manage the quality of the contained liquid, it is indispensable to ascertain the oxygen content in the headspace within the container, and the amount of oxygen dissolved in the fluid. As a devices to measure the amount of oxygen used in this kind of application, there has been a proposal for a device in which a headspace oxygen measuring device and a device for measuring the amount oxygen dissolved in the fluid are arranged in a sampling line that branches from the production line, canning containers are suitably pulled from the production line to the sampling line, samples of headspace gas and the contained fluid are extracted by piercing that canning container with needles or nozzles from the respective measuring devices, and the oxygen content is measured by analyzing these samples (for example, refer to Patent Publication 1). In addition, there have been various proposals for methods and devices to extract gas or fluid samples by piercing hermetically sealed contains such as cans (for example, refer to Patent Publications 2 to 4). Electro-chemical oxygen concentration meters, for example, polarograph-type oxygen concentration meters, which lead the oxygen in the sample between electrodes, cause a chemical response, and detect the oxygen based on the current flowing between the electrodes, have been used as means to detect the concentration of oxygen within samples (refer to Patent Publications 3 and 4).

Concentration meters that use the paramagnetism of the oxygen, and concentration meters that use fluorescent material are well-known as oxygen concentration meters that differ from electrochemical oxygen concentration meters. The latter concentration meter utilizes the phenomenon that the fluorescent energy that the fluorescent substance generates is consumed as the excitation energy of the ground state oxygen present around that fluorescent substance, thus quenching the fluorescent light, and the oxygen concentration is specified from the intensity and duration of the fluorescent light. Well-known as this type of concentration meter are concentration meters, in which a fluorescent substance is arranged on the tip of a probe, the fluorescent substance is irradiated with excitation light though optical fibers to produce fluorescent light, and this fluorescent light is led by optical fibers to a photo-electric conversion circuit positioned behind (for example, refer to Patent Publication 5). Moreover, examples of applications of oxygen concentration meters using fluorescent light include a proposal for a device to measure the required amount of biological oxygen in sample water by inserting a ride guide provided with a fluorescent oxygen tip into a culturing container filled with sample water (refer to Patent Publication 6).

[Patent Publication 1] Japanese Laid-open Patent No. H7-58244
[Patent Publication 2] U.S. Pat. No. 3,600,697
[Patent Publication 3] Japanese Laid-open Patent No. H1-113659
[Patent Publication 4] Japanese Laid-open Patent No. H4-176636
[Patent Publication 5] Japanese Laid-open Patent No. H10-132742
[Patent Publication 6] Japanese Laid-open Patent No. H11-242025

DISCLOSURE OF THE INVENTION

Problems To Be Solved By The Invention

In a conventional device for measuring oxygen concentration in hermetically sealed containers using an electro-chemical oxygen concentration meter it requires a time span of approximately 30 seconds to take a measurement. Moreover, because gas or interior fluid is taken from the hermetically sealed container as a sample and the oxygen inside that sample is consumed in the measurement, the conditions inside the hermetically sealed container change by extracting either the gas inside the headspace or the interior fluid, and there is concern that the other sample cannot be correctly measured. Consequently, it is necessary to separate the measurement of headspace oxygen content from the measurement of interior fluid dissolved oxygen content, and in addition to making the measurement labor intensive, it also requires the provision of dual measuring devices with one for headspace and the other for internal fluid. It is also inconvenient that measurements are not possible if a sufficient quantity of sample cannot be extracted. Meanwhile, oxygen concentration meters utilizing fluorescent light have the advantages that rapid, highly precise measurements of oxygen concentration can be made without consuming the sample.

Means To Resolve The Problems

An object of the present invention is to offer a method that can efficiently measure the oxygen content of both the headspace and fluid within a hermetically sealed container by taking advantage of the characteristics of a fluorescent-type oxygen concentration meter, and to offer a piercing device suitable to that measurement method.

In order to achieve the aforementioned object according to the oxygen content measurement method of one aspect of the present invention, the problem described above is resolved by a hermetically sealed container oxygen content measurement method, which detects fluorescent light generated from fluorescent substance on the tip of a probe, uses a fluorescent oxygen concentration meter to measure the oxygen content around the aforementioned fluorescent substance based on the results of that detection, and measures the oxygen content within a hermetically sealed container filled with fluid, comprising the steps of:

piercing the aforementioned container in the sealed state from the outside using a hollow needle with the tip of said hollow needle removed, and making the aforementioned interior space continuous with the headspace within the aforementioned container;

inserting the aforementioned probe through the aforementioned hollow needle to the aforementioned interior of the container; positioning the aforementioned fluorescent material in the headspace within the aforementioned container, and measuring the oxygen concentration of said headspace; and inserting the aforementioned probe further so that the aforementioned fluorescent material is submerged in the fluid inside the aforementioned container, and measuring the dissolved oxygen concentration inside the aforementioned fluid.

According to the aforementioned oxygen content measurement method, by successively sending the fluorescent substance on the tip of the probe through the hollow needle into the headspace and fluid, it is possible to rapidly measure the oxygen concentrations of the headspace and fluid respectively, and to calculate the oxygen content from the oxygen concentration obtained and the volume of the headspace or the volume of the fluid. With a fluorescent oxygen concentration meter it is not necessary for either the headspace gas or the fluid inside the container to be extracted outside the container as samples, and no oxygen is consumed in the measurement of the oxygen concentration; therefore the oxygen contents in the headspace and fluid can be measured continuously. Consequently, the measurement efficiency is superior, operator labor is reduced, and the configuration of the device required to measure the oxygen content is also simplified. Measurements are possible even if the there is little headspace volume, specifically, highly precise oxygen content measurements can be taken even with small-content containers.

In one aspect of the oxygen content measurement method of the present invention, further steps may be comprised of:

measuring the pressure within the aforementioned headspace through the aforementioned hollow needle;

measuring the pressure of a fixed volume tank;

measuring the pressure of the aforementioned headspace by making the aforementioned tank continuous with the aforementioned headspace through the aforementioned hollow needle after measuring the oxygen concentration of the aforementioned fluid; and calculating the volume of the aforementioned headspace volume from the measured pressures and the volume of the aforementioned tank.

According to this aspect, if we let Vh be the volume of the headspace; Va, the volume of the tank; Ph, the pressure of headspace prior to continuity; and Pah, the pressure of the tank after continuity, the relationship of $$Pah \times (Va+Vh) = Ph \times Vh + Pa \times Va \tag{1}$$

is established, and because only the headspace volume Vh is unknown in equation (1), the volume of the headspace can be calculated using the relationship of equation (1). Then, the oxygen content of the headspace can be calculated from the volume and concentration of the headspace. In terms of the dissolved oxygen content of the fluid, either the quantity of fluid to be filled as stipulated in the quantitative filling process is taken as the volume of fluid, or the difference derived by subtracting the headspace volume from the volume of the container is taken as the volume of the fluid, and then the dissolved oxygen content can be calculated from this volume and the oxygen concentration. The pressure of the headspace is measured through the hollow needle, or the headspace can be directly calculated following the measurement of the oxygen concentration because the tank and the fluid are made continuous through the hollow needle. Consequently, the measurement efficiency is heightened, the labor required for measurement is reduced, and the configuration of equipment required for measurement is simplified.

According to the container piercing device of one aspect of the present invention, the problem described above is resolved by comprising: a hollow needle, with an interior space into which the probe of a fluorescent oxygen concentration meter can be inserted, and with a tip that can pierce into a hermetically sealed container; means for sealing that seals the interior space of the aforementioned hollow needle from the outside when removing the tip of said hollow needle; means for detecting container interior pressure that detects the pressure of the interior space of the aforementioned hollow needle; a tank of a fixed volume connected with said interior space of said hollow needle; a tank valve that switches between forming and blocking the continuity between the aforementioned tank and the aforementioned interior space of the hollow needle; and means for detecting tank interior pressure that detects the aforementioned tank pressure when the continuity is blocked in relation to the aforementioned interior space of the aforementioned hollow needle.

According to the aforementioned piercing device, it is possible to measure the oxygen content of the headspace and the fluid respectively by piercing the container with the hollow needle while the interior space of the hollow needle is sealed from the outside by the sealing means, the tip of the hollow needle is inserted into the headspace part of the container, and successively arranging the fluorescent substance of the tip of the probe into the headspace and into the fluid in the container through that hollow needle. By detecting the tank interior pressure and the pressure of the interior space of the hollow needle respectively when the tank does not have continuity with the interior space of the hollow needle, and then detecting the pressure of the interior space of the hollow needle right after the tank and the interior space of the hollow needle have continuity, it is possible to measure the pressure of the gas enclosed in the interior of the headspace, the pressure of the tank when the continuity is blocked, and the pressure of the headspace when the tank and the headspace have continuity. Because the tank volume is fixed and already known, the volume of the headspace can be calculated from the measured values of these pressures and the tank volume using the aforementioned equation (1).

In one aspect of the piercing device of the present invention, a pressure detection line is connected to the aforementioned interior space of the aforementioned hollow needle; a first on-off valve and a second on-off valve, which is positioned farther away from the aforementioned hollow needle than the aforementioned first on-off valve, are connected to the aforementioned pressure detection line; the aforementioned tank is connected to the aforementioned pressure detection line between the first and second on-off valves; the aforementioned tank valve is arranged between the aforementioned pressure detection line and the aforementioned tank; and a manometer, which is jointly used as the aforementioned container interior pressure detection means and as the aforementioned tank interior pressure detection means, is connected between the aforementioned first and second on-off valves.

According to the aforementioned aspect, by respectively closing the second on-off valve and the tank valve, and by opening the first on-off valve, the pressure of the headspace gas can be measured by the manometer while preventing the exhaust of pressure from the interior space of the hollow needle to the outside or to the tank. Moreover, with the first on-off valve closed, opening the second on-off valve and the tank valve adjusts the pressure inside the tank through the second on-off valve and the tank valve, and by detecting that pressure with a manometer the interior pressure of the tank when the connection is blocked can be measured with the manometer. Further, with the second on-off valve closed, opening the first on-off valve and the tank valve connects the tank and the headspace of the container through the interior space of the hollow needle, and the headspace pressure when connected can be measured with a manometer. In this aspect, when the gas supply source (41) is connected farther away from the aforementioned hollow needle than the aforementioned second on-off valve, pressure can be filled into the tank and easily measured.

In one aspect of the piercing device of the present invention, a purge flow line for introducing an inert gas to the aforementioned interior space of the aforementioned hollow needle is also connected, and the piercing device is further provided with a valve mechanism to open and close the aforementioned purge flow line. According to this aspect, the oxygen is purged (expulsed) by filling the interior space of the hollow needle with an inert gas prior to piercing the container with the hollow needle, and the discharge of headspace pressure from the purge flow line can be prevented by using the valve mechanism to close the purge flow line when measuring the oxygen concentration. It is thereby possible to eliminate the affect of oxygen in the interior space of the hollow needle on measurement precision, and to conduct highly precise oxygen concentration measurements.

In one aspect of the piercing device of the present invention, a purge flow line for introducing inert gas to the pressure detection line and to the aforementioned interior space is connected to the aforementioned interior space of the aforementioned hollow needle; a first on-off valve and a second on-off valve, which is positioned farther from the aforementioned hollow needle than the aforementioned first on-off valve, may be connected to the aforementioned pressure detection line; the aforementioned tank is connected to the aforementioned pressure detection line between the aforementioned first and second valves; the aforementioned tank valve is arranged between the aforementioned pressure detection line and the aforementioned tank; a manometer, which is jointly used as the aforementioned container interior pressure detection means and as the aforementioned tank interior pressure detection means, is connected between the aforementioned first and second on-off valves; an inert gas supply source is connected farther from the aforementioned hollow needle than the aforementioned second on-off valve; the aforementioned inert gas supply source is also connected to the aforementioned purge flow line through the aforementioned valve mechanism; and a valve mechanism to open and close the aforementioned purge flow line t-may be further provided.

According to this aspect, as previously explained regarding the aspects above, it is possible to purge the oxygen in the interior space of the hollow needle utilizing the purge flow line and valve mechanism, and to calculate the headspace volume by detecting respectively: the headspace pressure when receiving continuity by the switching operation of the first and second on-off valves and the tank valve; the tank pressure; and the headspace pressure when connected. Further, it is not necessary to provide a separate gas supply source for purging oxygen and a gas supply source for measuring the headspace volume, which simplifies the configuration of the piercing device and makes it possible to reduce the operating costs thereof.

BRIEF EXPLANATION OF THE DIAGRAMS

BEST MODE FOR CARRYING OUT THE INVENTION

Figure 1:
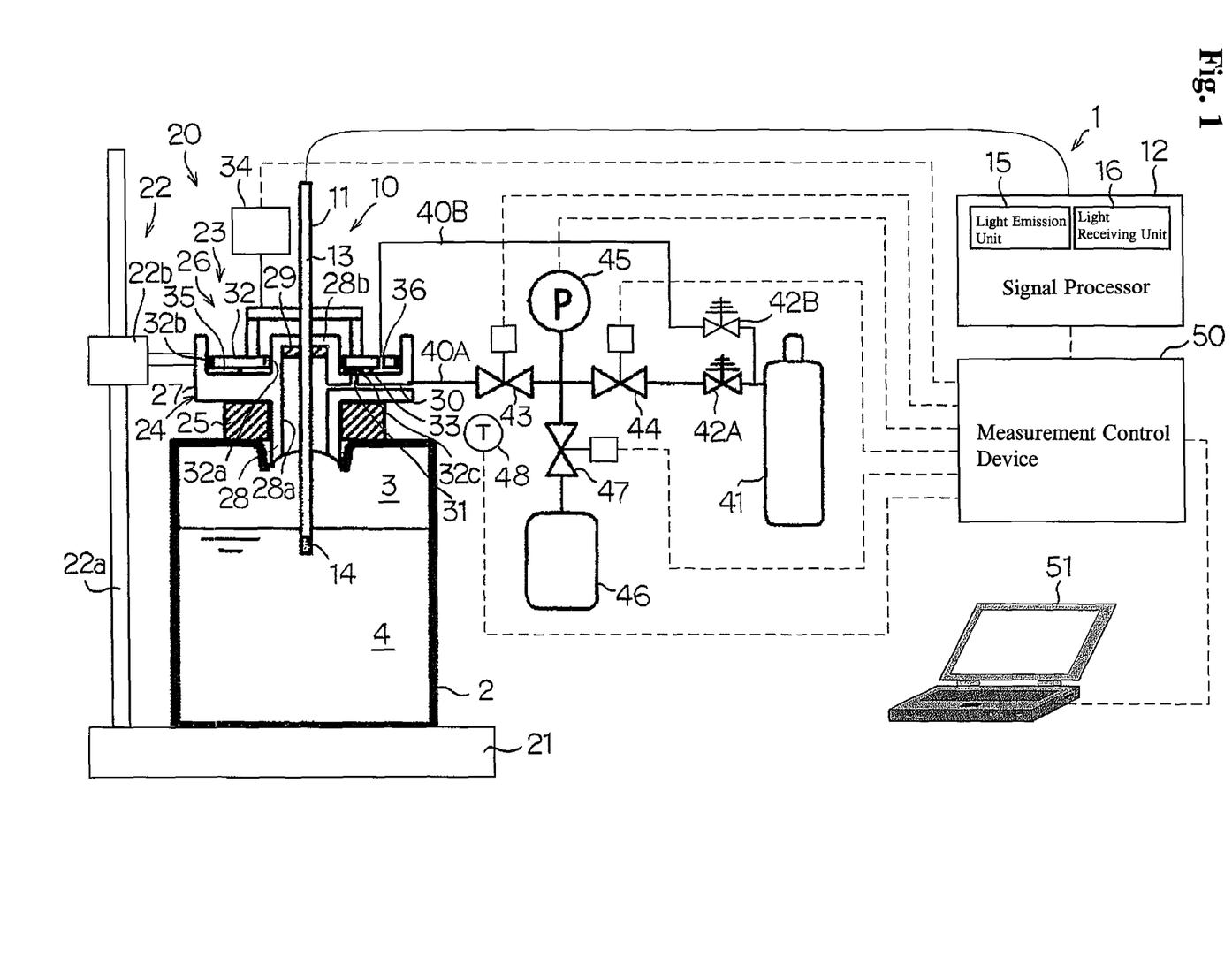
FIG. 1 is a diagram indicating the configuration of an oxygen concentration measuring device related to one aspect of the present invention.

FIG. 1 indicates the schematic configuration of an oxygen concentration measuring device for use in a measurement method related to one aspect of the present invention. This oxygen concentration measuring device 1 is for the purpose of measuring the oxygen contents respectively of a headspace 3 and a fluid 4 present in a hermetically sealed container 2, and is comprised of a fluorescent oxygen concentration meter 10, and a piercing device 20 for utilizing this oxygen concentration meter 10 for measuring the oxygen concentration within the container 2. Further, it is assumed that the container 2 in FIG. 1 is a can container.

The oxygen concentration meter 10 comprises a probe 11 and a signal processor 12. The probe 11 comprises an optical fiber cable 13 and a sensor tip 14 provided on the tip of that optical fiber cable 13. The optical fiber cable 13 extends from the end of the sensor tip 14 to the signal processor 12. The sensor tip 14 comprises a fluorescent substance that generates fluorescent light in response to irradiation by an excitation light of a specified wavelength (for example, UV light). For example, ruthenium metal complex and polycyclic aromatic hydrocarbons may be used as the fluorescent substance.

The signal processor 12 comprises a light emission unit 15 and a light receiving unit 16. The light emission unit 15 irradiates the fluorescent substance with excitation light facing the optical fiber cable 13. The light receiving unit 16 receives the fluorescent light of the sensor tip 14 that is transmitted through the optical fiber cable 13. The signal processor 12 causes irradiation of excitation light, which is sine wave light of a wave length that excites the fluorescent substance of the sensor tip 14, from the light emission unit 15 to the optical fiber [cable] 13. In addition, the signal processor 12 not only photoelectrically converts the fluorescent light that the light receiving unit 16 receives and creates intensity signals corresponding to the intensity of that fluorescent light, but also detects the phase difference between the sine wave light sent from the light emitting unit 15 and the fluorescent light received by the light receiving unit 16, and creates a delay time signal corresponding to the light quenching time of the fluorescent light. In an environment where oxygen molecules in the base state are present around the sensor tip 14, a light quenching phenomenon is produced, wherein the fluorescent energy is consumed by the excitation of the oxygen molecules, and the fluorescent light is quenched. The fluorescent light intensity and the quenching time of the fluorescent light (delay time), have a correlation with the oxygen concentration, and if the fluorescent light intensity and the quenching time of the fluorescent light have been determined, it is possible to measure the oxygen concentration around the sensor tip 14 using these values. The oxygen concentration meter 10 of the present aspect measures the oxygen concentration (or partial pressure) based on this principle.

The intensity signals and delay time signals created by the signal processor 12 are sent through a measurement control device 50 to a personal computer 51 (abbreviated PC hereinafter) for data processing. The functions of the measurement control device 50 and the PC 51 will be described later.

The piercing device 20 comprises a support stand 21 that supports the container 2, a guide mechanism 22 that is provided on the support stand 21, and a head unit 23 that is supported so that the position can be adjusted up and down by the guide mechanism 22. The support stand 21 is provided to support the container 2 in a vertically standing state. Here, in order to guarantee the depth in the up and down directions of the headspace, the support stand 21 may be configured so that the container 2 can be supported at a slant. The guide mechanism 22 comprises a guide rod 22a that extends up and down, and a slider 22b that can move up and down along that guide rod 22a. The head unit 23 is assembled on the slider 22b. Further, the slider 22b is securable at an option position on the guide rod 22a using a securing means not indicated in the diagram. A clamp bolt or a variety of other means may be used as the securing means. An operator may manually move the slider 22b up and down, or this may be achieved by the force of an actuator such as a motor or gas cylinder apparatus.

The head unit 23 comprises a head 24, a seal ring 25 provided on the lower surface of the head 24, and a valve mechanism 26 provided on the upper surface of the head 24. As indicated in detail in FIG. 2, a roughly disk-shaped head main unit 27 and a hollow needle 28, which is provided along the central line of that head main unit 27, are comprised. The previously described slider 22b of the guide mechanism 22 connects with the head main unit 27.

The hollow needle 28 protrudes below the head main unit 27, and a knife edge shape is formed on the tip (at the lower edge of the diagram) so that the top surface of the container 2 can be pierced. An interior space 28a of the hollow needle 28 is opened in the interior circumference of the tip of that hollow needle 28. The seal ring 25 is provided so as to entirely encircle the outer circumference of the hollow needle 28. A probe guide 28b is provided on the upper edge of the hollow needle 28 so as to cover the inner space 28a. The probe 11 is inserted into the inner space 28a of the hollow needle 28 through the center of that probe guide 28b. A seal ring 29 that seals the outer circumference of the probe 11 is provided on the lower surface of the probe guide 28b. A gas flow circuit 30 that reaches from the outer circumferential surface of the head main unit 27 to the inner space 28a of the hollow needle 28 is formed on the head 24. Further, a continuity hole 31 that opens to a circular groove 27a (FIG. 2) on the upper surface of the head main unit 27 is connected to the gas flow line 30.

Figure 2:
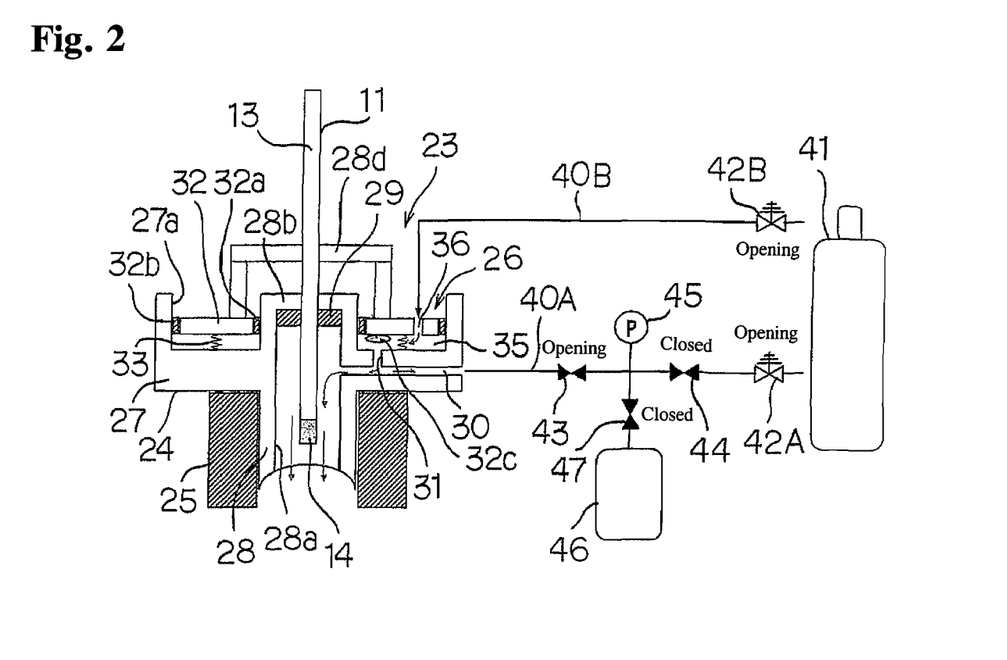
FIG. 2 is a diagram indicating the state prior to beginning measurements.

A valve mechanism 26 comprises a ring-shaped valve unit 32 that meshes with the circular groove 27a of the head main unit 27, a spring 33 that energizes the valve unit 32 upward, and an actuator 34 (indicated only in FIG. 1) that presses down and drives the valve unit 32. Seal rings 32a and 32b, which make close contact respectively with the inner and outer circumferential surfaces of the circular groove 27a, are provided on the inner and outer circumferences of the valve unit 32. A gas chamber 35 is thereby formed between the valve unit 32 and the head main unit 27. Moreover, provided on the lower surface of the valve unit 32 matching the position of the continuity hole 31 is a seal member 32c that is made from an elastic material. Further, a gas introduction line 36 that connects through to the gas chamber 35 is formed on the head main unit 27. The valve mechanism 26 above uses the actuator 34 to press in on the head main unit 27 and plug the continuity hole 31 with the seal member 32c of the valve unit 32, and blocks the continuity between the gas introduction line 36 and the interior space 28a of the hollow needle 28. When releasing the pressure of the actuator 34 on the head main unit 27, the valve unit 32 is pushed up by the spring 33, the seal member 32c is separated from the continuity hole 31, and the gas introduction line 36 thereby makes continuity with the interior space 28a of the hollow needle 28. Further, a cylindrical boss 32d is provided at the center of the valve unit 32, and the probe 11 also passes through the boss 32d and is inserted into the hollow needle 28.

As indicated in FIG. 1, the gas flow line 30 and the gas introduction line 36 of the head unit 23 are connected respectively with the gas cylinder through conduit lines 40A and 40B. Inert gas which does not contain oxygen, for example, nitrogen gas, is stored in the gas cylinder 41. Manual on-off valves 42A and 42B are provided respectively on conduit lines 40A and 40B. In addition, electromagnetic first on-off valve 43 and second on-off valve 44 are connected to the conduit line 40A that is connected to the gas flow line 30. The second on-off valve 44 is positioned farther from the hollow needle 28 than the first on-off valve 43. A manometer 45 and an accumulator tank 46 are connected between the on-off valves 43 and 44. The manometer 45 detects pressure between the on-off valves 43 and 44, and outputs this to a measurement control device 50. The accumulator tank 46 is a fixed volume steel bodied tank. An electromagnetic tank valve 47 is further connected between the accumulator tank 46 and the conduit line 40A. A thermometer 48 is arranged near the head unit 23. The thermometer 48 detects the temperature near the head unit 23, and outputs this to the measurement control device 50. Further, drawings of the thermometer have been omitted from FIG. 2 and after.

The measurement control device 50 outputs the fluorescent light intensity signals and delay time signals output from the signal processor 12, the pressure signals output from the manometer 45, and the temperature signals output from the thermometer 48 respectively in a format readable by the PC 51, and following the measurement trigger signals given from the PC 51, valve mechanism 26 of the piercing device 20, and the on-off valves 43, 44, and 47 are driven to open and close following a specified sequence. The PC 51 calculates the oxygen concentration (or partial pressure) corresponding to the intensity signals and delay time signals from the signal processor 12 by operating according to a program installed in the memory device thereof. By providing this kind of function, the measurement control device 50 and the PC 51 function as parts of the oxygen concentration meter 10. A variety of commercially available fluorescent oxygen meters may be utilized as this kind of fluorescent oxygen concentration meter 10. As an example, the fluorescent oxygen concentration meter and accessory application program that the German company PreSens offers under the trade mark of Microx TX3 can be utilized.

In addition, the PC 51 comprises the function of using the pressure detected by the manometer 45 to derive the volume of the headspace 3 of the container 2, the function of calculating the oxygen content present in the headspace 3 from the volume and oxygen concentration of the headspace 3, and the function of calculating the amount of oxygen dissolved in the contained fluid 4 from the volume and oxygen concentration of the contained fluid 4. These functions will be explained with measurement procedures that are described below. Here, the oxygen content means the quantity of oxygen per unit volume, and, for example, the units may be in mg/L.

Next, the oxygen concentration measurement procedures using the oxygen concentration measurement device 1 will be explained while referring to FIGS. 2 to 7. First, as indicated in FIG. 2, prior to beginning measurements with the head 24 separated and above the container 2 (not indicated in FIG. 2), the manual on-off valves 42A, 42B and the on-off valve 43 of the conduit line 40A are opened, while the on-off valve 44 and the tank valve 47 are closed. In this state, the valve unit 32 of the valve mechanism 26 is drawn back, and the continuity hole 31 is made continuous with the interior space 28a of the hollow needle 28. Inert gas is thereby led from the conduit line 40B through the continuity hole 31 and the gas flow line 30 to the interior space 28a of the hollow needle 28, the inert gas is led from the gas flow line 30 to the conduit line 40A up to the manometer 45, and the oxygen in these lines is purged with inert gas.

Figure 3:
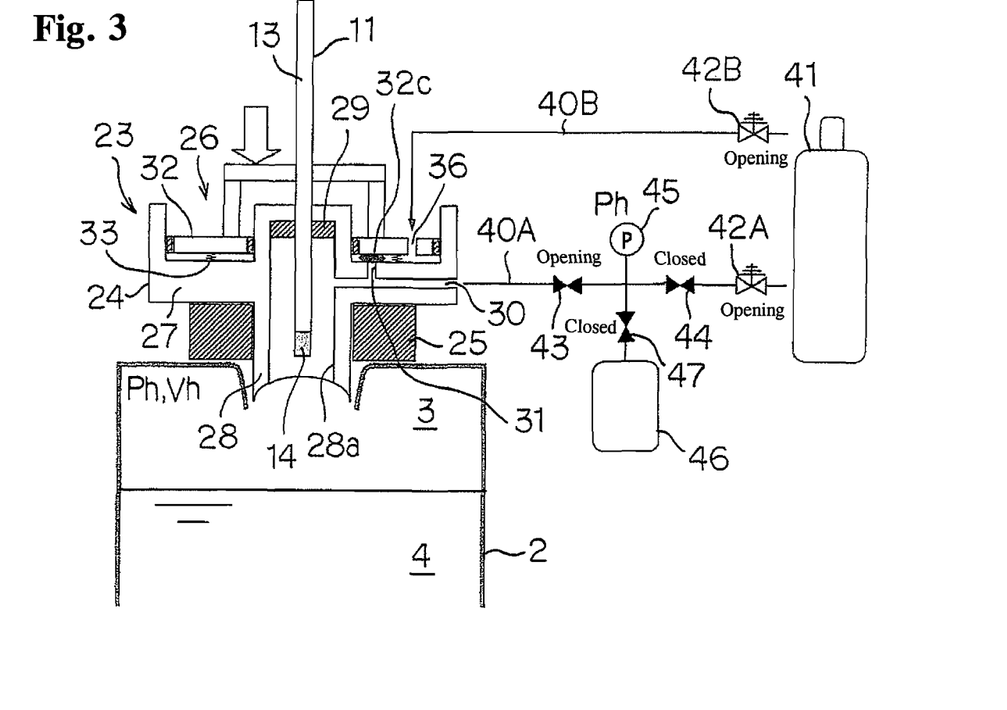
FIG. 3 is a diagram indicating the process of piercing a container.

After thoroughly purging the oxygen, the valve unit 32 of the valve mechanism 26 is depressed, thereby plugging the continuity hole 31 as indicated in FIG. 3, and the supply of inert gas to the interior space 28a of the hollow needle 28 is ended. Next, the head 24 is lowered facing the container 2, the hollow needle 28 pierces the top surface of the container 2, a hole is thereby punched in the container 2, and the interior space 28a of the hollow needle 28 is made continuous with the headspace 3. At that time, the seal ring 25 makes close contact with the container 2 and seals around the entire outer circumference of the hollow needle 28, thereby preventing the intrusion of outside air through the punched hole part, or the leaking of gas from the headspace 3. Further, the sensor tip 14 on the tip of the probe 11 is positioned in the hollow needle 28 at the time of punching the hole, and the penetration part of the probe 11 is sealed against the head 24 by the seal ring 29. The state of the on-off valves 42A, 42B, 43, and 44, and the tank valve 47 is as indicated in FIG. 2. The pressure Ph (equivalent to the interior pressure of the hollow needle 28) of the headspace 3 is introduced to the manometer by piercing the container 2, and this pressure Ph is transmitted to and recorded by the PC 51. Moreover, the temperature detected by the thermometer 48 is transmitted to and recorded by the PC 51 at the beginning of the measurement.

Figure 4:
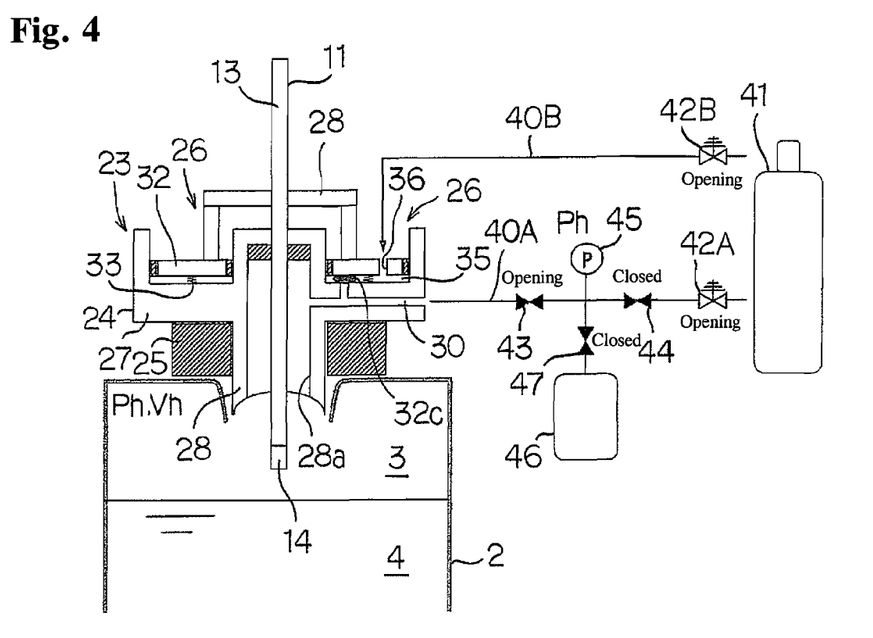
FIG. 4 is a diagram indicating the process of measuring the headspace oxygen concentration of the container.

After piercing the container 2 and while maintaining the valve mechanism 26, the on-off valves 42A, 42B, 43, and 44, and the tank valve 47 in the state indicated in FIG. 3, the probe 11 is lowered and the sensor tip 14 is positioned at the headspace 3 as indicated in FIG. 4. The oxygen concentration of the headspace 3 is measured in this state by utilizing the oxygen concentration meter 10. Further, the pressure of the headspace 3 is measured, and the oxygen concentration may be derived by utilizing the pressure Ph and temperature T of the headspace 3.

Figure 5:
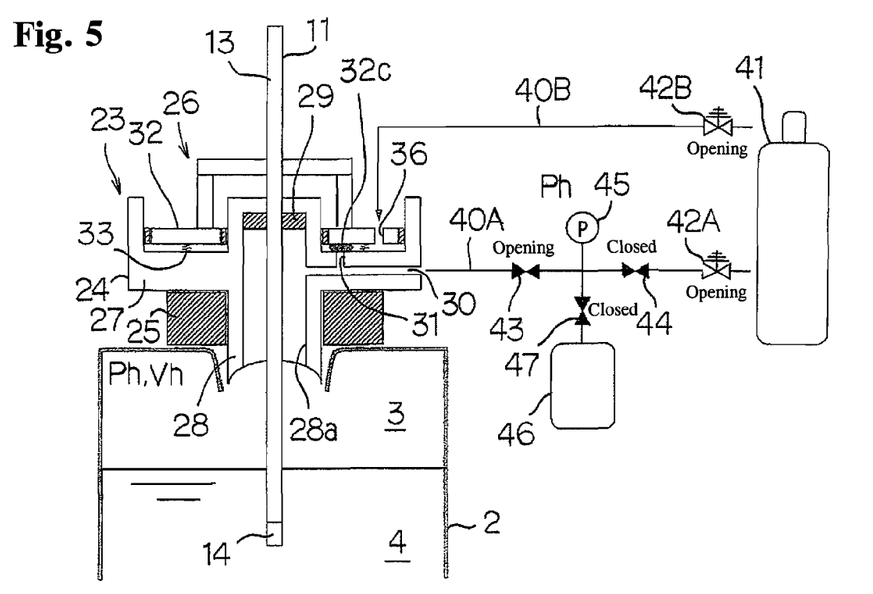
FIG. 5 is a diagram indicating the process of measuring oxygen concentration of the fluid inside the container.

After measuring the oxygen concentration of the headspace 3, next, the probe 11 is lowered further as indicated in FIG. 5, the sensor tip 14 is immersed in the contained fluid 4, and the oxygen concentration of the contained fluid 4 is measured by the oxygen concentration meter 10. In this case as well, the oxygen concentration of the contained fluid 4 may be derived by utilizing the pressure Ph and temperature T of the headspace 3. Further, valve mechanism 26, the on-off valves 42A, 42B, 43, and 44, and the tank valve 47 are maintained in a state like that indicated in FIG. 3.

Figure 6:
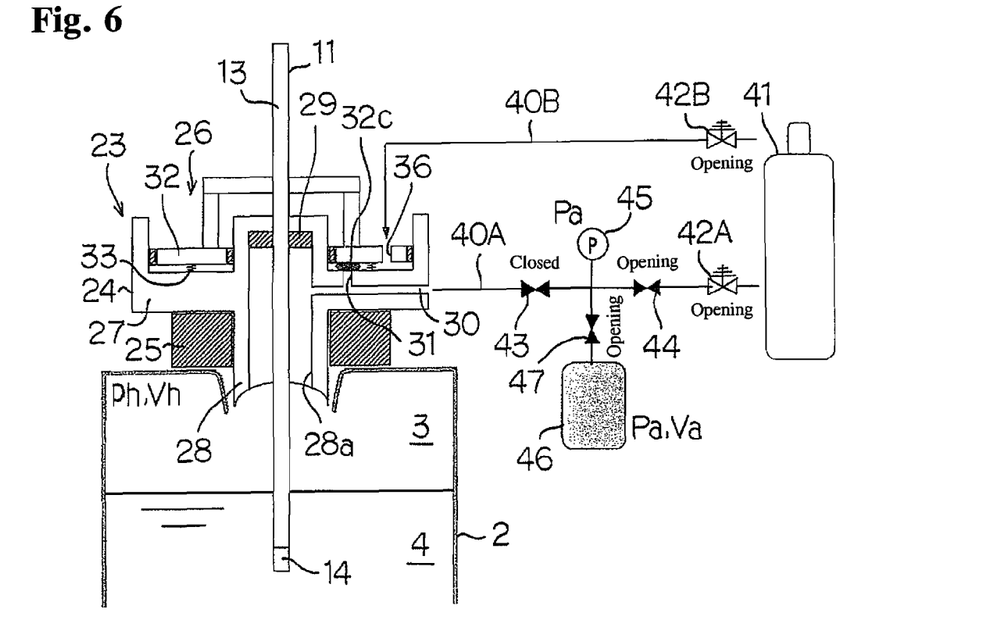
FIG. 6 is a diagram indicating the state when accumulating pressure in the accumulator tank in preparation for measuring the headspace volume.
Figure 7:
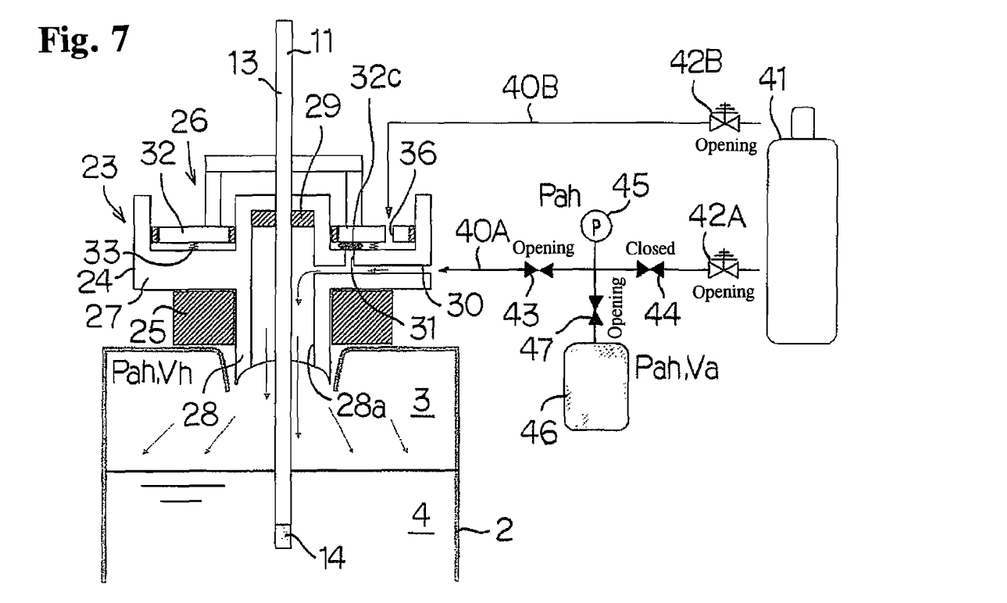
FIG. 7 is a diagram indicating the state when connecting the accumulator tank and the headspace, and measuring the pressure.

After measuring the oxygen concentration of the contained fluid 4, the on-off valve 43 of the conduit line 40A is closed as indicated in FIG. 6, the on-off valve 44 and the tank valve 47 are opened, and the inert gas is accumulated in the accumulator tank 46 just to a specified pressure. At that time, the pressure Pa of the tank 46 is introduced to the manometer 45, and that pressure Pa is transmitted to and recorded by the PC 51. Next, the on-off valve 44 is closed as indicated in FIG. 7, the on-off valve 43 is opened, and the accumulator tank and the headspace 3 are made continuous. Since the pressures of the accumulator tank 46 and the headspace 3 are thereby equalized, that pressure Pah is detected by the manometer 45, and is transmitted to and recorded by the PC 51. Then, the PC 51 calculates the volume Vh of the headspace 3 using the previously recorded pressure Ph of the headspace 3, the pressure of the inert gas accumulated in the accumulator 46, the pressure Pah when the accumulator tank 46 and the headspace 3 have continuity, and the volume Va of the accumulator 46 to fulfill the relationship of the equation (1) described above.

After the oxygen concentrations respectively of the headspace 3 and the contained fluid 4, and the volume and the temperature of the headspace 3 have been measured as described above, the oxygen content of the headspace 3 and the dissolved oxygen content of the contained fluid 4 are calculated respectively by the PC 51. Specifically, regarding the oxygen content of the headspace 3, the oxygen content per unit volume can be derived from the oxygen concentration of the headspace 3 detected by the oxygen concentration meter 10 and the volume Vh of the headspace 3. Regarding the dissolved oxygen content of the contained fluid 4, the oxygen content per unit volume can be derived from the oxygen concentration of the contained fluid 4 detected by the oxygen concentration meter 10 and the volume of the contained fluid 4. Regarding the volume of the contained fluid 4, it may be assumed that quantitative filling was realized in the process of filling the container 2 with the contained fluid 4, and thus the stipulated content to be filled in that filling process may be used as the volume of the contained fluid 4. Or, if it is reasonable to consider the volume of the container 2 to be invariable because the contained substance does not cause the container 2 to undergo plastic deformation, etc., then the value derived by subtracting the volume of the headspace 3 from the volume of the container 2 may be considered the volume of the contained fluid 4.

The respective oxygen contents of the headspace 3 and the contained fluid 4 that have been derived as described above are processed into a graph, etc. by the PC 51 and are presented to the user. The data processing of the oxygen contents obtained may be suitably stipulated.

In the embodiment above, the cylinder 25, valve mechanism 26, second on-off valve 44, and tank valve 47 function as seal means to seal the interior space 28a of the hollow needle 28, and the manometer 45 functions as container interior pressure detection means and tank interior pressure detection means. Moreover, the pressure detection line is comprised by a combination of the continuity hole 31, gas flow line 30, and conduit line 40A, and the purge flow line is comprised by the combination of the conduit line 40B, gas introduction line 36, gas chamber 35, gas flow line 30, and continuity hole 31. Here, of course, the configurations of the pressure detection line and the purge flow lines may be suitably modified.

The present invention is not limited to the aspects described above, and may be implemented in a variety of aspects. For example, the on-off valves 43 and 44 and the tank valve 47 may be valves that are manually switched by an operator. In the aspect indicated in the diagram, the pressure Ph of the headspace 3 and the pressure Pa of the accumulator tank 46 are both detected by the manometer 45, but these may be detected by separate pressure detection means. For example, the pressure Ph in the headspace 3 may be detected by embedding a pressure sensor in the interior space 28a of the hollow needle 28, while the pressure Pa of the tank may be detected by connecting a separate manometer to the accumulator tank 46. With a pressure sensor to detect the interior pressure of the hollow needle 28 arranged in the head 24, and with the accumulator tank 46 connected to the gas flow line 30 of the head 24 through the tank valve 47, that connection route may provide a route to adjust the pressure of accumulator tank 46 using a separate system. For pressure detection, in short, there may be means to detect the pressure enclosed in the interior space 28a of the hollow needle 28 and the headspace 3 when the hollow needle 28 has pierced the container 2, and means to detect the pressure inside the accumulator tank 46. If the volume of the headspace 3 and the volume of the fluid inside the container 2 are already known, the process of measuring the volume of the headspace 3 may be omitted. If the measurement of the oxygen content is implemented in an environment where a fixed room temperature is maintained, the thermometer 48 may be omitted.

The container targeted for measurement by the present invention is not limited to a can container, and as long as punching is possible by piercing with the hollow needle, a variety of containers may be targeted. For example, it is possible to use the measurement method of the present invention even with bottle-like containers, such as glass vials, by piercing the stopper with the hollow needle. In addition, it is possible to use the present invention to measure the oxygen content in a variety of hermetically sealed containers such as containers made of resin or paper, etc. In the above aspect, the oxygen content was derived as the quantity of oxygen per unit volume, but the present invention may be used even when derived as the quantities of oxygen contained in the headspace of the container and in the fluid of the container, or as the oxygen content of the volume as is.

The invention claimed is:

1. A hermetically sealed container oxygen content measurement method, which detects fluorescent light generated from fluorescent substance on the tip of a probe, uses a fluorescent oxygen concentration meter to measure the oxygen content around said fluorescent substance based on the results of that detection, and measures the oxygen content within a hermetically sealed container filled with fluid, comprising the steps of:
    piercing said container using a hollow needle with the interior space closed off from the outside and the tip of said hollow needle removed, and making said interior space continuous with the headspace within said container;
    inserting said probe through said hollow needle into said container interior;
    positioning said fluorescent material in the headspace within said container, and measuring the oxygen concentration of said headspace; and
    inserting said probe further so that said fluorescent material is submerged in the fluid inside said container, and measuring the dissolved oxygen concentration inside said fluid.

2. A hermetically sealed container oxygen content measurement method, which detects fluorescent light generated from fluorescent substance on the tip of a probe, uses a fluorescent oxygen concentration meter to measure the oxygen content around said fluorescent substance based on the results of that detection, and measures the oxygen content within a hermetically sealed container filled with fluid, comprising the steps of:
    piercing said container using a hollow needle with the interior space closed off from the outside and the tip of said hollow needle removed, and making said interior space continuous with the headspace within said container;
    inserting said probe through said hollow needle into said container interior;
    positioning said fluorescent material in the headspace within said container, and measuring the oxygen concentration of said headspace;
    measuring the pressure within said headspace through said hollow needle;
    measuring the pressure of a fixed volume tank;
    measuring the pressure of said headspace by making said tank continuous with said headspace through said hollow needle after measuring the oxygen concentration of said fluid;
    calculating the volume of said headspace volume from the measured pressures and the volume of said tank; and
    inserting said probe further so that said fluorescent material is submerged in the fluid inside said container, and measuring the dissolved oxygen concentration inside said fluid.

3. A container piercing device comprising:
    a hollow needle, with an interior space into which the probe of a fluorescent oxygen concentration meter can be inserted, and with a tip that can pierce into a hermetically sealed container;
    means for sealing that seals off the interior space of said hollow needle from the outside when removing the tip of said hollow needle;
    means for detecting container interior pressure that detects the pressure of the interior space of said hollow needle;
    a tank of a fixed volume connected with said interior space of said hollow needle;
    a tank valve that switches between forming and blocking the continuity between said tank and said interior space of said hollow needle; and
    means for detecting tank interior pressure that detects said tank pressure when continuity with said interior space of said hollow needle is blocked.

4. The piercing device according to claim 3, wherein a purge flow line for introducing an inert gas to said interior space of said hollow needle is also connected, and the piercing device is further provided with a valve mechanism to open and close said purge flow line.

5. The piercing device according to claim 3, wherein a purge flow line for introducing inert gas to the pressure detection line and to said interior space is connected to said interior space of said hollow needle;
    a first on-off valve and a second on-off valve, which is positioned farther from said hollow needle than said first on-off valve, are connected to said pressure detection line;
    said tank is connected to said pressure detection line between said first and second valves; said tank valve is arranged between said pressure detection line and said tank;
    a manometer, which is jointly used as said container interior pressure detection means and as said tank interior pressure detection means, is connected between said first and second on-off valves; an inert gas supply source is connected farther from said hollow needle than said second on-off valve;

said inert gas supply source is also connected to said purge flow line through said valve mechanism; and a valve mechanism to open and close said purge flow line is further provided.

6. The piercing device according to claim 3, wherein a pressure detection line is connected to said interior space of said hollow needle;

a first on-off valve and a second on-off valve, which is positioned farther away from said hollow needle than said first on-off valve, are connected to said pressure detection line;

said tank is connected to said pressure detection line between, the first and second on-off valves;

said tank valve is arranged between said pressure detection line and said tank; and a manometer, which is jointly used as said container interior pressure detection means and as said tank interior pressure detection means, is connected between said first and second on-off valves.

7. The piercing device according to claim 6, wherein a gas supply source is connected farther away from said hollow needle than said second on-off valve.

* * * * *